US009390510B2

(12) United States Patent
Lee et al.

(10) Patent No.: US 9,390,510 B2
(45) Date of Patent: Jul. 12, 2016

(54) METHOD, APPARATUS, AND SYSTEM FOR OUTPUTTING INFORMATION OF BLOOD FLOW INCLUDED IN REGION OF INTEREST BASED ON SELECTION INFORMATION

(71) Applicant: SAMSUNG MEDISON CO., LTD., Hongcheon-gun, Gangwon-do (KR)

(72) Inventors: Jae-Keun Lee, Gangwon-do (KR); Dong-Seok Lee, Gangwon-do (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 0 days.

(21) Appl. No.: 14/444,565

(22) Filed: Jul. 28, 2014

(65) Prior Publication Data
US 2015/0254867 A1    Sep. 10, 2015

(30) Foreign Application Priority Data
Mar. 5, 2014    (KR) .......................... 10-2014-0026209

(51) Int. Cl.
*G06K 9/00*  (2006.01)
*G06T 7/00*  (2006.01)
*A61B 8/06*  (2006.01)
*A61B 8/00*  (2006.01)
*A61B 8/08*  (2006.01)

(52) U.S. Cl.
CPC ............... *G06T 7/0081* (2013.01); *A61B 8/06* (2013.01); *A61B 8/465* (2013.01); *A61B 8/469* (2013.01); *A61B 8/488* (2013.01); *A61B 8/5223* (2013.01); *G06K 9/0014* (2013.01); *A61B 8/468* (2013.01); *A61B 8/5292* (2013.01); *G06T 2207/10132* (2013.01); *G06T 2207/30104* (2013.01)

(58) Field of Classification Search
USPC ................................... 382/128–134
See application file for complete search history.

(56) References Cited

U.S. PATENT DOCUMENTS

| | | | | |
|---|---|---|---|---|
| 4,886,059 A | * | 12/1989 | Weber | 128/207.15 |
| 5,095,909 A | * | 3/1992 | Nakayama et al. | 600/442 |
| 5,148,809 A | * | 9/1992 | Biegeleisen-Knight et al. | 600/443 |
| 5,838,592 A | * | 11/1998 | Spratt | 702/155 |
| 5,928,153 A | * | 7/1999 | Chiang et al. | 600/454 |
| 6,610,014 B1 | | 8/2003 | Yamamoto et al. | |
| 8,047,993 B2 | * | 11/2011 | Shau et al. | 600/453 |
| 8,340,744 B2 | * | 12/2012 | Bredno et al. | 600/431 |
| 2001/0017937 A1 | * | 8/2001 | Bonnefous | 382/128 |
| 2006/0058610 A1 | * | 3/2006 | Olstad | 600/407 |

(Continued)

FOREIGN PATENT DOCUMENTS

WO    2009/013686 A2    1/2009

OTHER PUBLICATIONS

European Search Report dated Jul. 21, 2015 issued in European Patent Application No. 14171251.3.

*Primary Examiner* — Alex Liew
(74) *Attorney, Agent, or Firm* — McDermott Will & Emery LLP (57) ABSTRACT

Disclosed is an ultrasound image processing method. The ultrasound image processing method includes generating an ultrasound image indicating a region of interest (ROI) by using echo signals which corresponds to ultrasound waves irradiated onto the ROI, sequentially setting respective indexes in a plurality of blood flows included in the ROI detected based on the ultrasound image, determining blood flow corresponding to a selected index, based on an external signal for selecting one of the set indexes, and displaying information corresponding to the determined blood flow.

16 Claims, 6 Drawing Sheets

(56) References Cited

U.S. PATENT DOCUMENTS

| | | | |
|---|---|---|---|
| 2008/0269611 A1* | 10/2008 | Pedrizzetti et al. | 600/454 |
| 2009/0003675 A1* | 1/2009 | Moreau-Gobard | 382/131 |
| 2009/0074267 A1* | 3/2009 | Pedrizzetti et al. | 382/128 |
| 2010/0125204 A1 | 5/2010 | Yoo et al. | |
| 2010/0157041 A1* | 6/2010 | Klaiman ............... G06T 7/0022 348/77 | |
| 2010/0160764 A1* | 6/2010 | Steinberg et al. | 600/407 |
| 2010/0172556 A1* | 7/2010 | Cohen et al. | 382/128 |
| 2010/0274134 A1* | 10/2010 | Shyu et al. | 600/455 |
| 2010/0290693 A1* | 11/2010 | Cohen et al. | 382/134 |
| 2012/0225941 A1* | 9/2012 | Green | 514/549 |
| 2012/0253190 A1* | 10/2012 | Gauthier et al. | 600/431 |
| 2013/0046168 A1* | 2/2013 | Sui | 600/411 |
| 2013/0150717 A1* | 6/2013 | Sato | 600/441 |
| 2013/0163839 A1* | 6/2013 | Li et al. | 382/131 |
| 2013/0172755 A1* | 7/2013 | Kim et al. | 600/454 |
| 2015/0051488 A1* | 2/2015 | Matsumoto et al. | 600/438 |

* cited by examiner

METHOD, APPARATUS, AND SYSTEM FOR OUTPUTTING INFORMATION OF BLOOD FLOW INCLUDED IN REGION OF INTEREST BASED ON SELECTION INFORMATION

RELATED APPLICATIONS

This application claims the benefit of Korean Patent Application No. 10-2014-0026209, filed on Mar. 5, 2014, in the Korean Intellectual Property Office, the disclosure of which is incorporated herein in its entirety by reference.

BACKGROUND

1. Field

One or more embodiments of the present invention relate to a method, apparatus, and system for outputting information of blood flow included in a region of interest (ROI) based on selection information.

2. Description of the Related Art

A Doppler image generating apparatus irradiates an ultrasound wave onto an ROI, and measures a Doppler shift frequency of an echo signal reflected from blood flow included in the ROI, thereby detecting a distribution of blood flow in real time.

Recently, provided is technology in which the Doppler image generating apparatus automatically finds a position of blood flow included in an ROI to dispose a color box or a sample volume (SV) at the position, estimates an angle of the blood flow in which the color box or the sample volume is disposed, and adjusts a slope of the color box or an angle of the sample volume.

However, when blood flow included in an ROI shown in a Doppler image is provided in plurality, the Doppler image generating apparatus automatically disposes the color box or the sample volume in blood flow where an amount of blood flow is the largest, and for this reason, it is difficult to acquire information of blood flow desired by a user.

SUMMARY

One or more embodiments of the present invention include a method, apparatus, and system for outputting information of blood flow included in an ROI based on selection information.

One or more embodiments of the present invention include a non-transitory computer-readable storage medium storing a program for executing the method in a computer.

Additional aspects will be set forth in part in the description which follows and, in part, will be apparent from the description, or may be learned by practice of the presented embodiments.

According to one or more embodiments of the present invention, an ultrasound image processing method includes: generating an ultrasound image indicating a region of interest (ROI) by using echo signals which corresponds to ultrasound waves irradiated onto the ROI; sequentially setting respective indexes in a plurality of blood flows included in the ROI detected based on the ultrasound image; determining blood flow corresponding to a selected index, based on an external signal for selecting one of the set indexes; and displaying information corresponding to the determined blood flow.

According to one or more embodiments of the present invention, provided is a non-transitory computer-readable storage medium storing a program for executing the ultrasound image processing method in a computer.

According to one or more embodiments of the present invention, an ultrasound image processing apparatus includes: a generation unit that generates an ultrasound image indicating a region of interest (ROI) by using echo signals which corresponds to ultrasound waves irradiated onto the ROI; a setting unit that sequentially sets respective indexes in a plurality of blood flows included in the ROI detected based on the ultrasound image; a determination unit that determines blood flow corresponding to a selected index, based on an external signal for selecting one of the set indexes; and a display unit that displays information corresponding to the determined blood flow.

According to one or more embodiments of the present invention, an ultrasound diagnostic system includes: a probe that irradiates ultrasound waves onto a region of interest (ROI) included in an object, and receives echo signals which corresponds to an ultrasound wave; and an image processing apparatus that generates an ultrasound image indicating the ROI by using the echo signal, sequentially sets respective indexes in a plurality of blood flows included in the ROI detected based on the ultrasound image, determines blood flow corresponding to a selected index, based on an external signal for selecting one of the set indexes, and displays information corresponding to the determined blood flow.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list.

Figure 1:
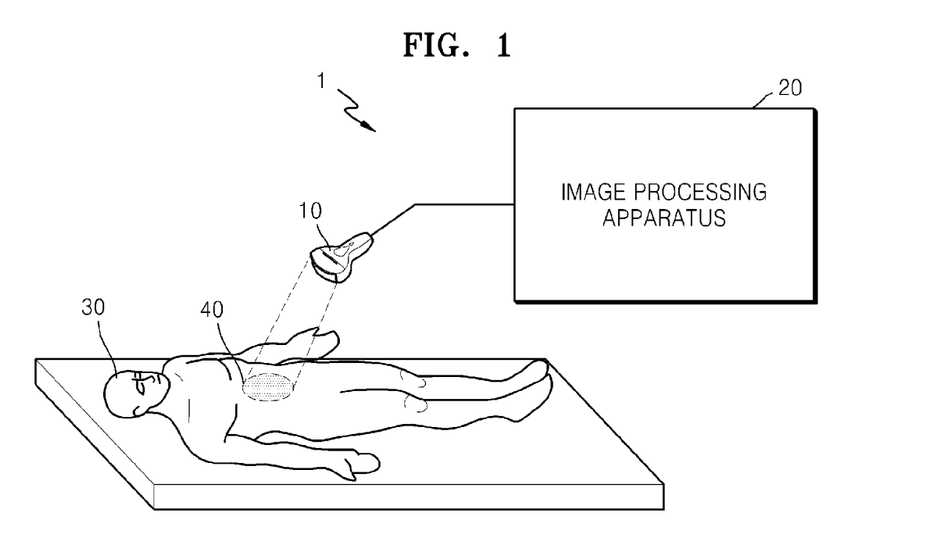
FIG. 1 is a configuration diagram illustrating an example of an ultrasound diagnostic system according to an embodiment.

FIG. 1 is a configuration diagram illustrating an example of an ultrasound diagnostic system 1 according to an embodiment.

Referring to FIG. 1, the ultrasound diagnostic system 1 includes a probe 10 and an image processing apparatus 20. The ultrasound diagnostic system 1 of FIG. 1 is illustrated as including only elements associated with the present embodiment. Therefore, it may be understood by those skilled in the art that the ultrasound diagnostic system 1 may further include general-use elements in addition to the elements of FIG. 1.

The probe 10 irradiates ultrasound waves onto an ROI 40 included in an object 30, and receives echo signals corresponding to the irradiated ultrasound wave. In other words, the probe 10 irradiates the ultrasound waves onto the ROI 40. The probe 10 receives the echo signals that are signals reflected from each of tissues included in the ROI 40. The probe 10 transmits the echo signals to a generation unit 210 included in the image processing apparatus 20.

Here, an ultrasound signal generating unit (not shown) of the image processing apparatus 20 may perform a transmission beamforming operation in consideration of a position and size of the ROI 40 to generate ultrasound waves which are irradiated by the probe 10. A detailed method of generating ultrasound waves irradiated by the probe 10 is obvious to one of ordinary skill in the art, and thus, its detailed description is not provided.

When a plurality of transducers (not shown) included in the probe 10 respectively irradiate ultrasound waves onto an internal certain part of the object 30, the ultrasound waves are partially reflected from layers between a plurality of tissues. In particular, the ultrasound waves may be reflected from parts (for example, blood cells of blood plasma, and small tissues of organs) in which a density is changed in the object 30. Reflected signals vibrate the transducers (not shown), which output electrical pulses based on the vibrations. The probe 10 transmits the electrical pulses to the generation unit 210.

Here, the object 30 denotes a target of which an image is to be generated, and for example, may be a patient. However, the present embodiment is not limited thereto. The ROI 40 denotes an internal certain region of the object 30 of which an image is generated, and for example, may be a region including a plurality of blood flows. However, the present embodiment is not limited thereto.

The image processing apparatus 20 generates an ultrasound image indicating the ROI 40 by using the echo signals transmitted from the probe 10. The image processing apparatus 20 detects a plurality of blood flows included in the ROI 40 on the basis of the generated ultrasound image, and sequentially sets respective indexes in the detected blood flows. The image processing apparatus 20 determines blood flow corresponding to a selected index on the basis of an external signal for selecting one of the indexes. Here, the external signal may be a signal which is input by a user by using an input device (not shown), which includes an input device, such as a knob button, a trackball, a mouse, a keyboard, or a touch screen, and a software module for driving the same. The image processing apparatus 20 displays information corresponding to the determined blood flow.

Hereinafter, a detailed operation of the image processing apparatus 20 will be described with reference to FIGS. 2 to 8.

Figure 2:
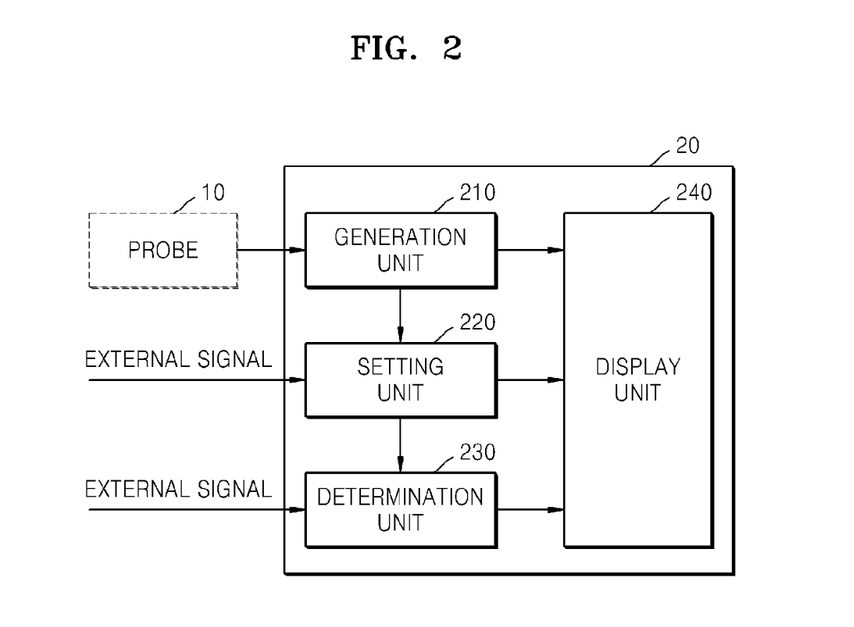
FIG. 2 is a block diagram illustrating an example of an image processing apparatus according to an embodiment.

FIG. 2 is a block diagram illustrating an example of the image processing apparatus 20 according to an embodiment.

Referring to FIG. 2, the image processing apparatus 20 includes a generation unit 210, a setting unit 220, a determination unit 230, and a display unit 240. The image processing apparatus 20 of FIG. 2 is illustrated as including only elements associated with the present embodiment. Therefore, it may be understood by those skilled in the art that the image processing apparatus 20 may further include general-use elements in addition to the elements of FIG. 2.

Moreover, it is well known to one of ordinary skill in the art that the display unit 240 of the image processing apparatus 20 of FIG. 2 may be provided as an independent image display apparatus. In other words, the display unit 240 may include an output device, which is provided in the ultrasound diagnostic system 1, such as a display panel or a monitor, and a software module for driving the same.

The generation unit 210, setting unit 220, and determination unit 230 of the image processing apparatus 20 of FIG. 2 may correspond to one or more processors. Each of the processors may be implemented as an array of a plurality of logic gates, or may be implemented as a combination of a general-use microprocessor and a memory that stores a program executable by the microprocessor. Also, it may be understood by one of ordinary skill in the art that the elements may be implemented as another type hardware.

The generation unit 210 generates an ultrasound image indicating the ROI 40 by using an echo signal corresponding to an ultrasound wave irradiated onto the ROI 40. In detail, the generation unit 210 analog-digital converts the echo signal (i.e., electrical pulses) transmitted from the probe 10 to generate a digital signal. The generation unit 210 performs reception beamforming of the digital signal to generate a reception focusing signal, and generates ultrasound data by using the reception focusing signal. Here, the ultrasound data may include an in-phase/quadrature (K)) signal, but is not limited thereto.

The generation unit 210 generates the ultrasound image indicating the ROI 40 by using the ultrasound data. Here, the ROI 40 denotes an internal certain region of the object 30 of which an image is generated, and for example, may be a region including a plurality of blood flows. However, the present embodiment is not limited thereto.

Here, an ultrasound image generated by the generation unit 210 denotes a Doppler mode image. In other words, the generation unit 210 acquires information about an amount of each of the blood flows included in the ROI 40 and information about a moving direction and speed of blood flow, by using the ultrasound data, and generates the Doppler mode image on the basis of the acquired information.

The setting unit 220 sequentially sets respective indexes in the plurality of blood flows included in the ROI 40 detected based on the ultrasound image. In other words, the setting unit 220 detects a plurality of blood flows included in the ROI 40 on the basis of the ultrasound image, and sequentially sets respective indexes in the detected plurality of blood flows.

For example, the setting unit 220 generates a reference for setting an index on the basis of the external signal. The setting unit 220 segments a plurality of blood flows from the ultrasound image. It is described that the reference for setting the index is generated and then the blood flows are segmented from the ultrasound image, but the present embodiment is not limited to the above-described sequence. In other words, the setting unit 220 may segment the blood flows from the ultrasound image before generating the reference for setting the index, and the above-described two operations may be simultaneously performed. Furthermore, the setting unit 220 aligns the segmented blood flows according to the generated reference, and sequentially sets respective indexes in the aligned blood flows. Hereinafter, an example in which the setting unit 220 operates will be described in detail.

The setting unit 220 generates the reference for setting the index on the basis of the external signal. Here, the index denotes a symbol for distinguishing and indicating each of a plurality of blood flows. For example, the index may be a numeral or a sign which is displayed at a position adjacent to blood flow, or may be different shapes or colors for distinguishing respective blood flows.

Information of the reference for setting the index may be input to the image processing apparatus 20 by a user by using the external signal. In other words, the external signal may be a signal which is input by a user by using an input device (not shown), which includes an input device, such as a knob button, a trackball, a mouse, a keyboard, or a touch screen, and a software module for driving the same.

Here, the reference for setting the index may be one of a blood flow speed, a blood flow direction, an amount of blood flow, and a position of blood flow included in an ultrasound image. For example, the setting unit 220 may generate, as the reference for setting the index, an ascending order of an average speed of blood flow (or the highest speed of the blood flow) or a descending order of the average speed of the blood flow (or the highest speed of the blood flow). Alternatively, the setting unit 220 may set an index by using only blood flows which flow in a predetermined direction among a plurality of blood flows. Alternatively, the setting unit 220 may generate, as the reference for setting the index, an ascending order of an amount of blood flow or a descending order of the amount of blood flow. Here, the setting unit 220 may determine the ascending order of the amount of blood flow or the descending order of the amount of blood flow in correspondence with the number of pixels indicating respective blood flows in the ultrasound image. Alternatively, the setting unit 220 may generate, as the reference for setting the index, a clockwise direction (or a counterclockwise direction) with respect to the center of the ultrasound image. Alternatively, the setting unit 220 may generate, as the reference for setting the index, a downward direction from a top, a right direction from the left, and an edge direction from the center in the ultrasound image. However, the reference generated by the setting unit 220 is not limited to the above-described examples, and all references for distinguishing and indicating each blood flow may be applied without being limited.

Moreover, the setting unit 220 may set a threshold value for the above-described reference on the basis of the external signal. For example, when it is assumed that the reference for setting the index is an average speed of blood flow, the setting unit 220 may set A cm/sec as the threshold value. Alternatively, when it is assumed that the reference for setting the index is an amount of blood flow, the setting unit 220 may set, as the threshold value, that the number of pixels corresponding to blood flow in the ultrasound image is a B number. Alternatively, when it is assumed that the reference for setting the index is a position of blood flow, the setting unit 220 may set, as the threshold value, that a radius with respect to the center of the ultrasound image is within C cm.

The setting unit 220 segments a plurality of blood flows from the ultrasound image. Hereinafter, an example in which the setting unit 220 segments a plurality of blood flows from an ultrasound image will be described in detail with reference to FIG. 3.

Figure 3:
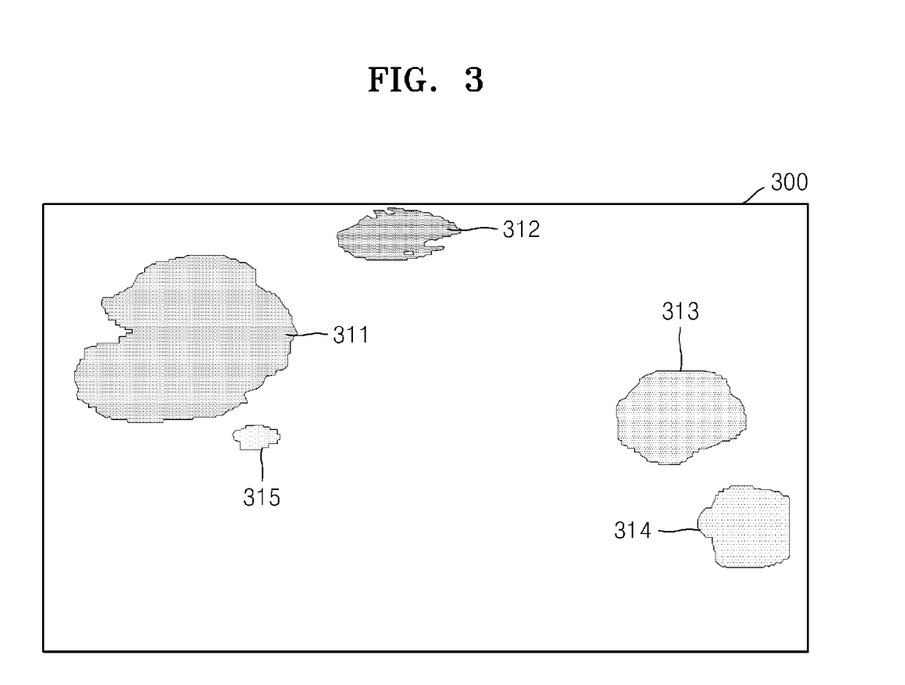
FIG. 3 is a diagram for describing an example in which a setting unit according to an embodiment segments a plurality of blood flows from an ultrasound image.

FIG. 3 is a diagram for describing an example in which the setting unit 220 according to an embodiment segments a plurality of blood flows from an ultrasound image.

Referring to FIG. 3, examples of blood flows 311 to 315 segmented from an ultrasound image 300 are illustrated. FIG. 3 illustrates a total of five the blood flows 311 to 315 included in the ROI 40, but the present embodiment is not limited thereto.

The setting unit 220 segments objects included in the ultrasound image 300. For example, the setting unit 220 may segment the objects from the ultrasound image 300 on the basis of a region growing method, but is not limited thereto.

Subsequently, the setting unit 220 extracts the objects 311 to 315 corresponding to blood flow from among the segmented objects. For example, when ultrasound data corresponding to each of the segmented objects includes formation about a moving direction or speed, the setting unit 220 determines that the segmented objects correspond to the blood flow, and extracts the segmented objects as the objects 311 to 315 corresponding to the blood flow.

Referring again to FIG. 2, the setting unit 220 aligns the segmented blood flows according to a generated reference, and sequentially sets respective indexes in the aligned blood flows. Hereinafter, an example in which the setting unit 220 sequentially sets respective indexes in blood flows will be described with reference to FIG. 4.

Figure 4:
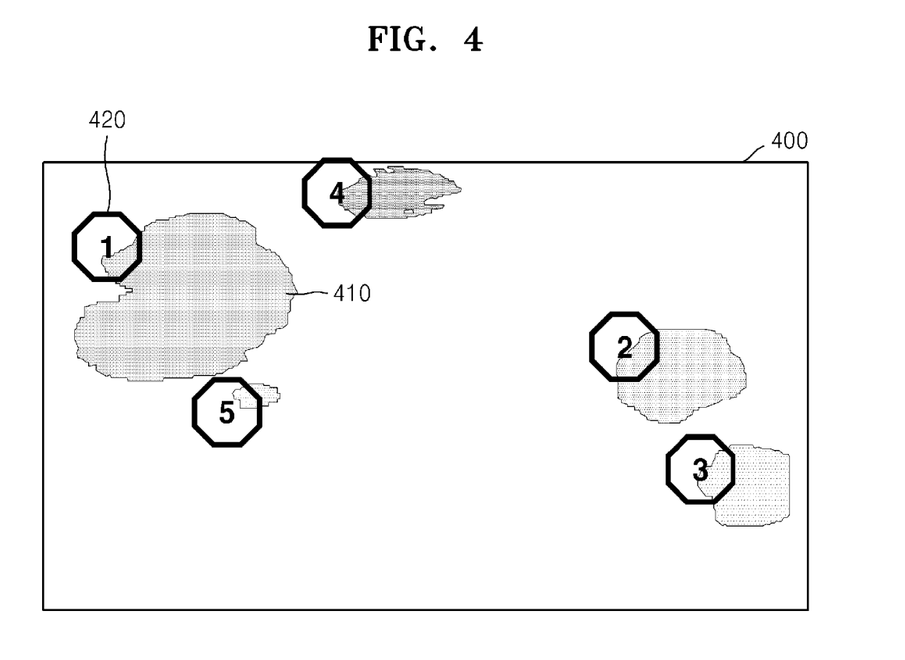
FIG. 4 is a diagram for describing an example in which the setting unit according to an embodiment sequentially sets indexes in respective blood flows.

FIG. 4 is a diagram for describing an example in which the setting unit 220 according to an embodiment sequentially sets indexes in respective blood flows.

Referring to FIG. 4, examples of blood flows segmented from an ultrasound image 400 are illustrated. In five blood flows illustrated in FIG. 4 the number of blood flows included in the ultrasound image 400 may be a total of five, and the number of blood flows equal to or greater than a threshold value among blood flows included in the ultrasound image 400 may be a total of five. In the following description, it is assumed that the setting unit 220 generates an index as a numeral, generates a reference for setting an index as an amount of blood flow, and sets, as a threshold value, that the number of pixels corresponding to blood flow in the ultrasound image 400 is a B number.

The setting unit 220 aligns a plurality of segmented blood flows according to a generated reference. For example, when it is assumed that the number of blood flows segmented from the ultrasound image 400 is a total of ten, the setting unit 220 aligns the ten blood flows in a descending order of an amount of blood flow. Subsequently, the setting unit 220 extracts only upper five blood flows in which the number of pixels corresponding to respective blood flows is equal to or more than the B number. Subsequently, the setting unit 220 sets an index in the order of 1→2→3→4→5 from blood flow having a largest amount of blood flow.

Referring again to FIG. 2, the display unit 240 displays the ultrasound image, generated by the generation unit 210, on a screen of the image processing apparatus 20. Also, the display unit 240 displays objects of a plurality of blood flows segmented from the ultrasound image and the index set by the setting unit 220, on a screen of the image processing apparatus 20. In other words, as illustrated in FIG. 4, the display unit 240 displays an index 420, set by the setting unit 220, at a position adjacent to a position of blood flow 410 corresponding thereto.

The determination unit 230 determines blood flow corresponding to a selected index on the basis of an external single that selects one index from among a plurality of set indexes. In other words, the determination unit 230 receives an external signal that selects one index from among indexes displayed by the display unit 240, and determines blood flow corresponding to a selected index on the basis of the received external signal. Hereinafter, an example in which the determination unit 230 determines blood flow corresponding to a selected index on the basis of an external signal will be described in detail with reference to FIG. 5.

Figure 5:
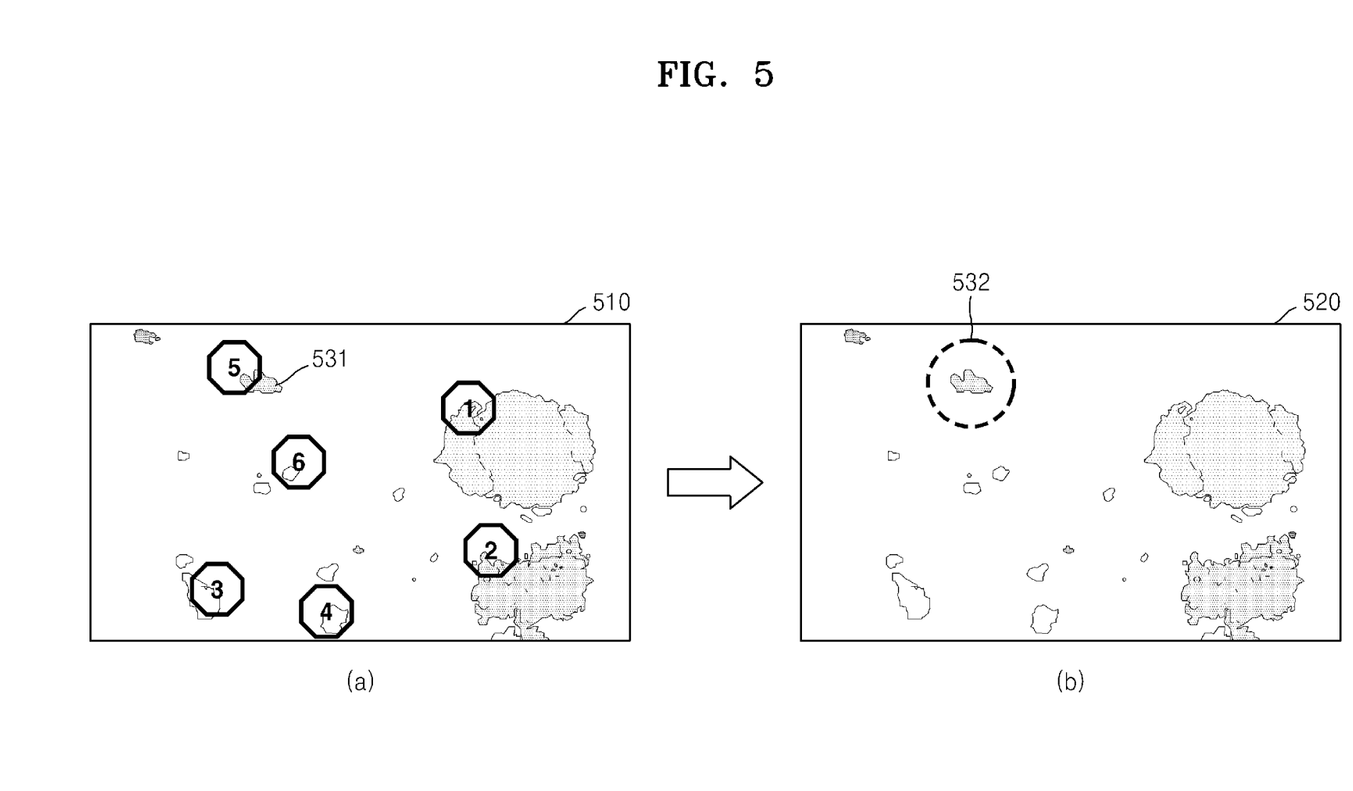
FIG. 5 is diagrams for describing an example in which a determination unit according to an embodiment determines blood flow.

FIG. 5 is diagrams for describing an example in which the determination unit 230 according to an embodiment determines blood flow.

In FIG. 5 (a), an example in which blood flows segmented from an ultrasound image 510 and an index is set in some of the blood flows is illustrated. In FIG. 5 (b), an example in which one of blood flows with an index set therein is determined is illustrated.

Referring to FIG. 5 (a), the setting unit 220 segments blood flows from the ultrasound image 510, and sets an index in all or some of the blood flows on the basis of a predetermined reference and threshold value. An example in which the setting unit 220 operates has been described above with reference to FIG. 4, and thus, its detailed description is not repeated.

The display unit 240 displays an index, set by the setting unit 220, at a position adjacent to a position of blood flow corresponding thereto, and a user inputs an external signal, which selects one index from among a plurality of displayed indexes, to the image processing apparatus 20. For example, the user may select one index from a plurality of indexes by using an input device such as a knob button, a trackball, a mouse, a keyboard, or a touch screen.

Referring to FIG. 5 (b), the determination unit 230 determines blood flow corresponding to an index on the basis of an external signal. For example, when it is assumed that an external signal is a signal which selects '5' from among the indexes illustrated in FIG. 5 (a), the determination unit 230 determines blood flow 532, corresponding to '5' among a plurality of blood flows displayed in an ultrasound image 520, as blood flow corresponding to the external signal.

Referring again to FIG. 2, the display unit 240 displays information, corresponding to determined blood flow, on a screen of the image processing apparatus 20. Here, the information corresponding to the determined blood flow denotes at least one or more of a position, direction, speed, and amount of the determined blood flow.

In other words, the display unit 240 distinguishes and displays blood flow, determined by the determination unit 230 from among a plurality of blood flows included in the ROI 40, and the other blood flows, and displays a position, direction, speed, or amount of blood flow determined by the determination unit 230. Hereinafter, an example in which the display unit 240 distinguishes and displays blood flow determined by the determination unit 230 and the other blood flows will be described in detail with reference FIG. 6.

Figure 6:
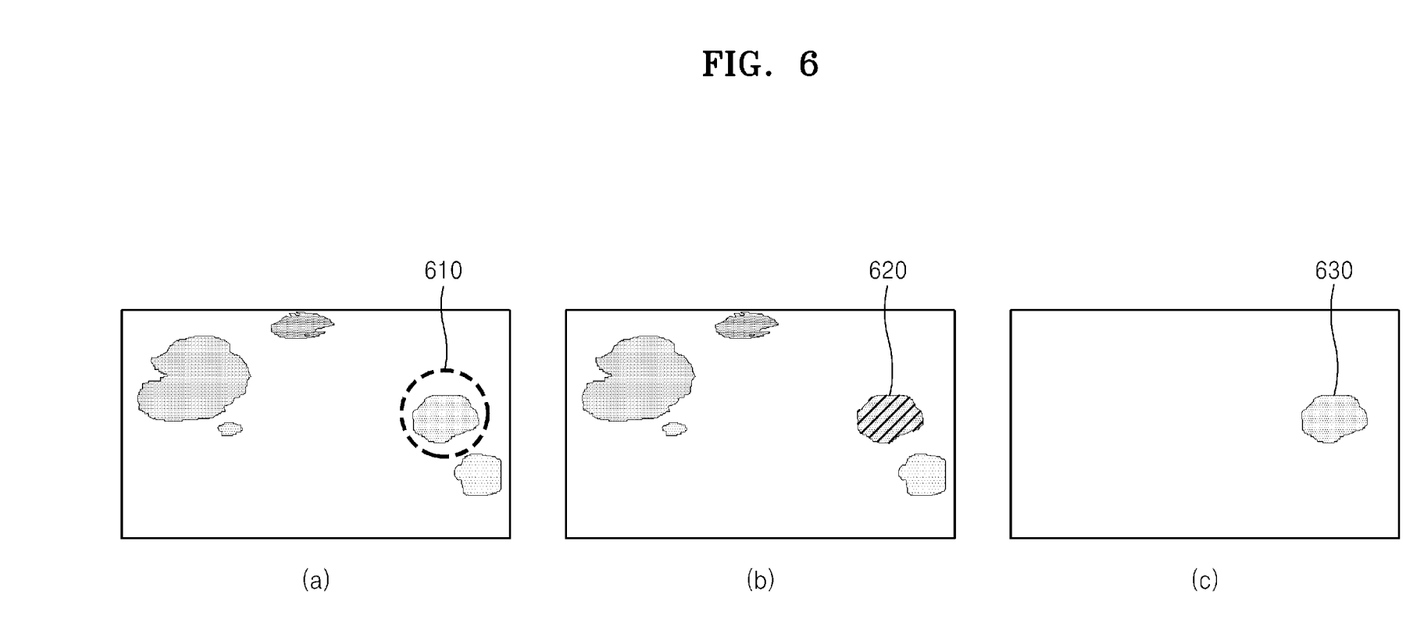
FIG. 6 is diagrams for describing an example in which a display unit according to an embodiment distinguishes and displays blood flow determined by the determination unit and the other blood flows.

FIG. 6 is diagrams for describing an example in which the display unit 240 according to an embodiment distinguishes and displays blood flow determined by the determination unit 230 and the other blood flows.

Referring to FIGS. 6 (a) to (c), an example in which the display unit 240 distinguishes and displays blood flows 610, 620 and 630 determined by the determination unit 230 and the other blood flows is illustrated. Referring to FIG. 6 (a), the display unit 240 may display a looped curve at an outer portion of the blood flow 610 determined by the determination unit 230, and thus distinguish and display the blood flow 610 and the other blood flows. Referring to FIG. 6 (b), the display unit 240 may display the blood flow 620 determined by the determination unit 230 in a certain shape or color, and thus distinguish and display the blood flow 620 and the other blood flows. Referring to FIG. 6 (c), the display unit 240 may display only the blood flow 630 determined by the determination unit 230 without displaying the other blood flows, and thus distinguish and display the blood flow 630 and the other blood flows.

Referring again to FIG. 2, the display unit 240 displays a position, direction, speed, or amount of blood flow determined by the determination unit 230. In detail, the display unit 240 extracts a position, direction, speed, or amount of the blood flow determined by determination unit 230 from among information about an amount of each of blood flows (included in the ROI 40 acquired by the generation unit 210) and information about a moving direction and speed of each blood flow, and displays the extraction result.

Figure 7:
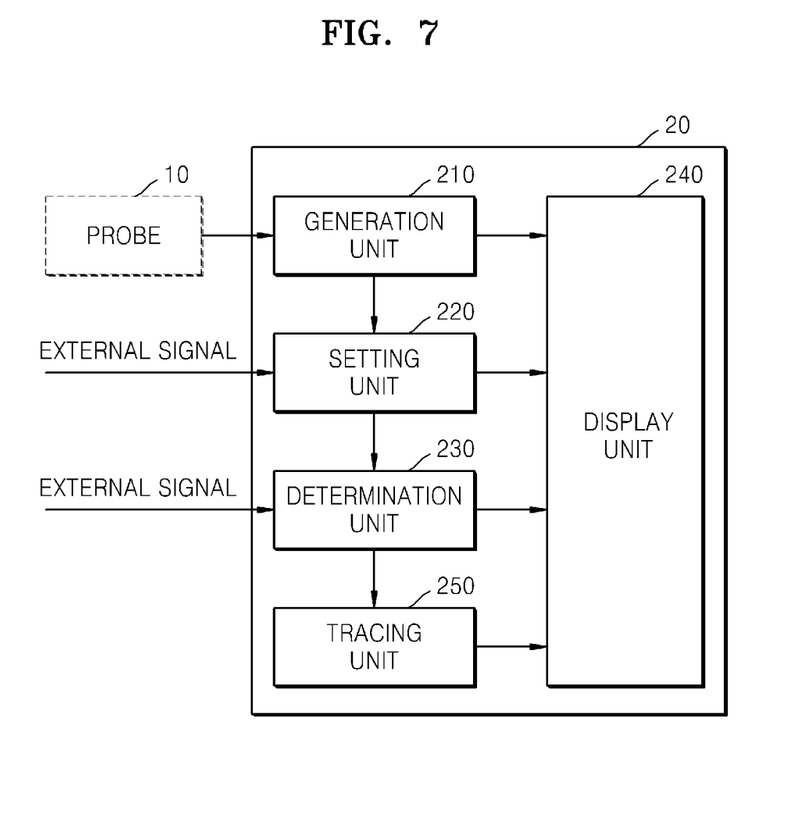
FIG. 7 is a block diagram illustrating another example of an image processing apparatus according to an embodiment.

FIG. 7 is a block diagram illustrating another example of an image processing apparatus 20 according to an embodiment.

Referring to FIG. 7, the image processing unit 20 includes a generation unit 210, a setting unit 220, a determination unit 230, a display unit 240, and a tracing unit 250. The image processing apparatus 20 of FIG. 7 is illustrated as including only elements associated with the present embodiment. Therefore, it may be understood by those skilled in the art that the image processing apparatus 20 may further include general-use elements in addition to the elements of FIG. 7.

Moreover, it is well known to one of ordinary skill in the art that the display unit 240 of the image processing apparatus 20 of FIG. 7 may be provided as an independent image display apparatus. In other words, the display unit 240 may include an output device, which is provided in the ultrasound diagnostic system 1, such as a display panel or a monitor, and a software module for driving the same.

Moreover, the generation unit 210, setting unit 220, determination unit 230, and tracing unit 250 of the image processing apparatus 20 of FIG. 7 may correspond to one or more processors. Each of the processors may be implemented as an array of a plurality of logic gates, or may be implemented as a combination of a general-use microprocessor and a memory that stores a program executable by the microprocessor. Also, it may be understood by one of ordinary skill in the art that the elements may be implemented as another type hardware.

Moreover, operations of the generation unit 210, setting unit 220, determination unit 230, and display unit 240 of the image processing apparatus 20 of FIG. 7 are as described above with reference to FIG. 2, and thus, their detailed descriptions are not repeated below.

The tracing unit 250 traces a position of blood flow which is changed with time. Here, blood flow of which a position is traced by the tracing unit 250 denotes blood flow determined by the determination unit 230.

A position of blood flow may be changed by a breath of the object 30 with time. In other words, a position of the blood flow at the maximum inhalation time of the object 30 may differ from that of the blood flow at the maximum exhalation time of the object 30. The tracing unit 250 may trace the position of the blood flow which is changed by a breath or fine movement of the object 30, and may accurately acquire information about a current position of the blood flow which is determined by the determination unit 230.

For example, the tracing unit 250 receives information about the position of the blood flow from the determination unit 230, and compares the received information with an ultrasound image of the ROI 40 which is transmitted from the generation unit 210 in real time. In detail, the tracing unit 250 sets a region having a radius of D mm with respect to the position of the blood flow determined by the determination unit 230, and sets a region, corresponding to the set region, in the ultrasound image which is transmitted from the generation unit 210 in real time. Here, the radius of D mm set by the tracing unit 250 may be preset by the image processing apparatus 20. Subsequently, the tracing unit 250 searches for the position of the blood flow, determined by the determination unit 230, in the region which is set in the ultrasound image, and transmits the search result (i.e., a current position of the blood flow) to the display unit 240.

Figure 8:
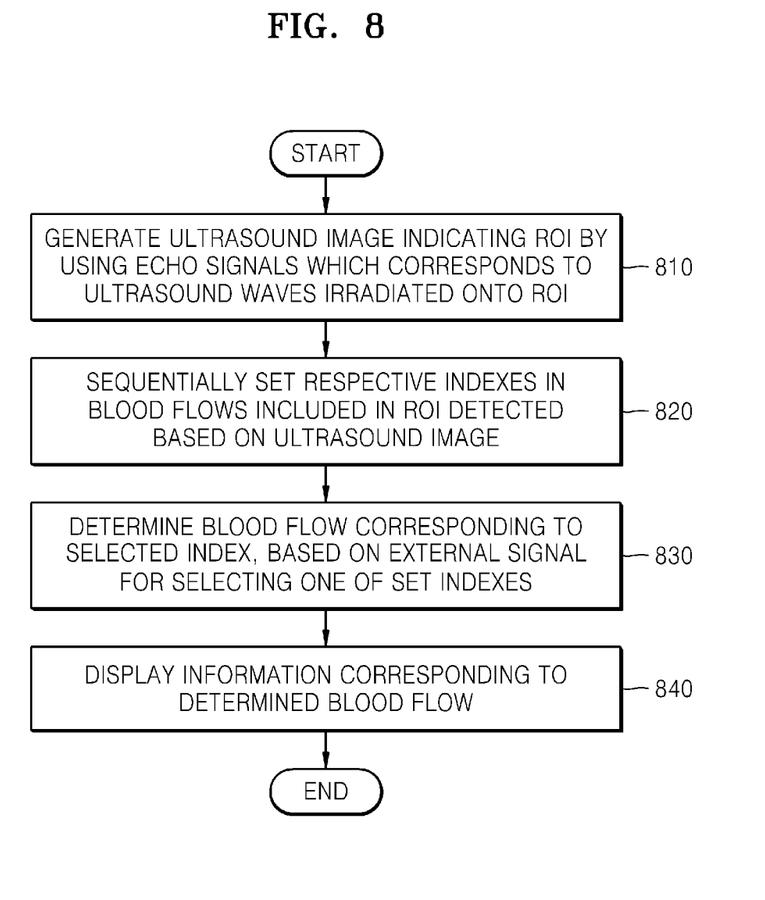
FIG. 8 is a flowchart illustrating an example of an ultrasound image processing method according to an embodiment.

FIG. 8 is a flowchart illustrating an example of an ultrasound image processing method according to an embodiment.

Referring to FIG. 8, the ultrasound image processing method includes a plurality of operations that are performed in a time series by the ultrasound diagnostic system 1 and image processing apparatus 20 of FIGS. 1, 2, and 7. Thus, although not described below, the above-described details of the ultrasound diagnostic system 1 and image processing apparatus 20 of FIGS. 1, 2, and 7 may be applied to the ultrasound image processing method of FIG. 8.

In operation 810, the generation unit 210 generates an ultrasound image indicating the ROI 40 by using an echo signal which corresponds to an ultrasound wave irradiated onto the ROI 40. Here, the ROI 40 denotes an internal certain region of the object 30 of which an image is generated, and for example, may be a region including a plurality of blood flows.

In operation 820, the setting unit 220 sequentially sets respective indexes in a plurality of blood flows included in the ROI 40 on the basis of the ultrasound image. Here, each of the indexes denotes a symbol for distinguishing and indicating each of the plurality of blood flows.

In operation 830, the determination unit 230 determines blood flow corresponding to a selected index on the basis of an external signal for selecting one of the set indexes. Here, the external signal may be a signal which is input by a user by using an input device (not shown), which includes an input device, such as a knob button, a trackball, a mouse, a keyboard, or a touch screen, and a software module for driving the same.

In operation 840, the display unit 240 displays information corresponding to the determined blood flow. Here, the information corresponding to the determined blood flow denotes at least one or more of a position, direction, speed, and amount of the determined blood flow.

As described above, according to the one or more of the above embodiments of the present invention, a plurality of indexes are sequentially and respectively set in a plurality of blood flows displayed on a screen, information of blood flow corresponding to one index selected from among the set plurality of indexes is output, and a user acquires information of desired blood flow among a plurality of blood flows included in an ROI.

Moreover, a position of blood flow which is changed due to a breath of an object is traced in real time, and thus, the user acquires accurate information of a blood flow speed.

The above-described method may be written as computer programs and may be implemented in general-use digital computers that execute the programs using a computer-readable recording medium. Data structure used in the above-described method may be recorded in a computer-readable recording medium by using various methods. Examples of the computer-readable recording medium include magnetic storage media (e.g., ROM, RAM, USB, floppy disks, hard disks, etc.) and storage media such as optical recording media (e.g., CD-ROMs, or DVDs).

It should be understood that the exemplary embodiments described herein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. An ultrasound image processing method comprising:
   generating an ultrasound image indicating a region of interest (ROI) by using echo signals which correspond to ultrasound waves irradiated onto the ROI;
   sequentially setting one respective index in each respective blood flow of a plurality of blood flows, wherein each of the plurality of blood flows indicates a blood flow of a different blood vessel, included in the ROI detected based on the ultrasound image;
   determining blood flow corresponding to a selected index, based on an external signal for selecting one of the set indexes; and
   displaying information corresponding to the determined blood flow.

2. The ultrasound image processing method of claim 1, wherein information corresponding to the determined blood flow comprises at least one of a position, direction, speed, and amount of the blood flow.

3. The ultrasound image processing method of claim 1, wherein the setting comprises:
   generating a reference for setting each of the indexes, based on an external signal;
   segmenting the plurality of blood flows from the ultrasound image, and aligning the segmented blood flows according to the generated reference; and
   sequentially setting the respective indexes in the aligned blood flows.

4. The ultrasound image processing method of claim 3, wherein the reference comprises at least one of a position, direction, speed, and amount of each of the blood flows in the ultrasound image.

5. The ultrasound image processing method of claim 1, wherein the determining comprises receiving an external signal which selects one index from among the indexes displayed on a screen, and determining blood flow corresponding to a selected index, based on the external signal.

6. The ultrasound image processing method of claim 1, further comprising tracing and displaying a position of the determined blood flow which is changed with time.

7. The ultrasound image processing method of claim 1, which the ultrasound image comprises a Doppler mode image.

8. A non-transitory computer-readable storage medium storing a program for executing the ultrasound image processing method of claim 1 in a computer.

9. An ultrasound image processing apparatus comprising:
   a generation unit that generates an ultrasound image indicating a region of interest (ROI) by using echo signals which corresponds to ultrasound waves irradiated onto the ROI;
   a setting unit that sequentially sets one respective index in each respective blood flow of a plurality of blood flows, wherein each of the plurality of blood flows indicates a blood flow of a different blood vessel, included in the ROI detected based on the ultrasound image;
   a determination unit that determines blood flow corresponding to a selected index, based on an external signal for selecting one of the set indexes; and
   a display unit that displays information corresponding to the determined blood flow.

10. The ultrasound image processing apparatus of claim 9, wherein information corresponding to the determined blood flow comprises at least one of a position, direction, speed, and amount of the blood flow.

11. The ultrasound image processing apparatus of claim 9, wherein the setting unit generates a reference for setting each of the indexes, based on an external signal, segments the plurality of blood flows from the ultrasound image, aligns the segmented blood flows according to the generated reference, and sequentially sets the respective indexes in the aligned blood flows.

12. The ultrasound image processing apparatus of claim 11, wherein the reference comprises at least one of a position, direction, speed, and amount of each of the blood flows in the ultrasound image.

13. The ultrasound image processing apparatus of claim 9, wherein the determination unit receives an external signal which selects one index from among the indexes displayed by the display unit, and determines blood flow corresponding to a selected index, based on the external signal.

14. The ultrasound image processing apparatus of claim 9, further comprising a tracing unit that traces a position of the determined blood flow which is changed with time.

15. The ultrasound image processing apparatus of claim 9, which the ultrasound image comprises a Doppler mode image.

16. An ultrasound diagnostic system comprising:
a probe that irradiates ultrasound waves onto a region of interest (ROI) included in an object, and receives echo signals which corresponds to an ultrasound wave; and
an image processing apparatus that generates an ultrasound image indicating the ROI by using the echo signal, sequentially sets one respective index in each respective blood flow of a plurality of blood flows, wherein each of the plurality of blood flows indicates a blood flow of a different blood vessel, included in the ROI detected based on the ultrasound image, determines blood flow corresponding to a selected index, based on an external signal for selecting one of the set indexes, and displays information corresponding to the determined blood flow.

* * * * *